United States Patent

Sheffield et al.

[11] Patent Number: 6,004,333
[45] Date of Patent: Dec. 21, 1999

[54] PROSTHETIC WITH COLLAGEN FOR TISSUE REPAIR

[75] Inventors: Warren D. Sheffield; Scott Wampler, both of Loveland; Jesse Kuhns, Cincinnati; Jeffrey J. Vaitekunas, West Chester, all of Ohio

[73] Assignee: Ethicon Endo-Surgery, Inc., Cincinnati, Ohio

[21] Appl. No.: 08/962,607

[22] Filed: Oct. 31, 1997

[51] Int. Cl.[6] ....................... A61B 17/04
[52] U.S. Cl. ............ 606/151; 602/41; 602/44; 602/48
[58] Field of Search ............ 606/151, 41, 44, 606/48

[56] References Cited

U.S. PATENT DOCUMENTS

| | | | |
|---|---|---|---|
| 2,671,444 | 3/1954 | Pease, Jr. | 606/151 |
| 3,272,204 | 9/1966 | Artandi et al. | 606/151 |
| 3,376,869 | 4/1968 | Borysko | 606/151 |
| 3,563,228 | 2/1971 | Seiderman | 128/1 |
| 5,209,776 | 5/1993 | Bass et al. | 106/124 |
| 5,246,156 | 9/1993 | Rothfuss et al. | 227/176 |
| 5,258,000 | 11/1993 | Gianturco | 606/151 |
| 5,290,296 | 3/1994 | Phillips | 606/144 |
| 5,290,297 | 3/1994 | Phillips | 606/144 |
| 5,470,010 | 11/1995 | Rothfuss et al. | 227/177 |
| 5,733,337 | 3/1998 | Carr, Jr. et al. | 623/11 |
| 5,824,015 | 10/1998 | Sawyer | 606/214 |

FOREIGN PATENT DOCUMENTS

| | | | |
|---|---|---|---|
| 0637452A1 | 2/1995 | European Pat. Off. | A61L 27/00 |
| WO 92/14513 | 9/1992 | WIPO | A61N 5/00 |
| WO 96/03925 | 1/1996 | WIPO | . |
| WO 96/07355 | 3/1996 | WIPO | A61B 17/00 |
| WO 96/09795 | 5/1996 | WIPO | . |

OTHER PUBLICATIONS

Okumura N., Teramachi M., Takimoto Y., Nakamura T., Ikada Y., Shimizu Y. (1994) Experimental Reconstructrion of the Intrathoracic Trachea Using a New Prosthesis Made from Collagen Grafted Mesh. ASAIO Journal. 40, No. 3:834–839.

P20056EP/CPM Mar. 11, 1999 EPO (Search Report).

Nerve injury associated with laparoscopic inguinal heriorrhapy, Prakash Sampath, MD, Charles J. Yeo, MD, and James N. Campbell, MD Baltimore MD Surgery, 1995; 118:829–33.

Laparoscopic Hernia Repair, Robert J. Fitzgibbones, Jr., M.D., F.A.C.S., J. Barry McKernan, M.D., Ph.D., F.A.C.S., Albert T. Spaw, M.D., F.A.C.S. Leonard S. Schultz M.D., F.A.C.S., Techniques in Endoscopic Surgery, Ethicon Endo-Surgery.

Primary Examiner—Gary Jackson
Attorney, Agent, or Firm—Louis J. Capezzuto

[57] ABSTRACT

A prosthetic for placement over a defect in tissue includes at least one collagen pad for placement on tissue surrounding the defect. A patch is placeable over the defect and the collagen pad wherein the collagen pad, the patch and the tissue are adhereable to each other upon an application of pressure and energy. Alternatively, the prosthetic can consist of a patch with at least one collagen pad integrally formed with the patch. Another alternative prosthetic includes a patch made of collagen throughout.

7 Claims, 5 Drawing Sheets

6,004,333

PROSTHETIC WITH COLLAGEN FOR TISSUE REPAIR

FIELD AND BACKGROUND OF THE INVENTION

The present invention relates, in general, to the surgical repair of tissue, and more particularly, to a new and useful method for repairing a defect in tissue such as an inguinal hernia and a novel prosthetic used in carrying out the method.

It is established practice in the surgical field to repair defects in tissue, for instance, an inguinal hernia, through the use of PROLENE™ mesh (manufactured and sold by Ethicon, Inc., Somerville, N.J.). Generally the mesh is cut to a desired size for placement over the inguinal hernia. Once the sized mesh has been placed over the defect, the mesh is attached to the surrounding inguinal tissue using several known attachment means.

Once the mesh is in place, it is important that the mesh serve as a barrier over the defect in order to restrict the lower viscera in the patient's abdomen from protruding through the defect. Accordingly, it is essential that the attachment means used to secure the mesh to the inguinal tissue have an initial strength of several pounds of force in both the tensile and shear directions. Moreover, it is important that the mesh remain in place for several days so that natural adhesions can form to ensure that the mesh is sufficiently anchored to the tissue.

One common way of attaching the mesh to tissue is through the use of suture and needle. As would be expected, the suturing technique for this procedure requires a great deal of skill and is normally conducted by very experienced surgeons, especially for minimally invasive or laparoscopic procedures. Since the learning curve for laparoscopic suturing is extremely steep, many surgeons are slow to adopt this technique.

In response to the challenges associated with suturing, other fastening techniques have evolved. Accordingly, it is now common practice to use a surgical stapler such as the ENDOSCOPIC MULTI-FIRE STAPLER™, (manufactured and sold by Ethicon Endo-Surgery, Inc., Cincinnati, Ohio). U.S. Pat. No. 5,470,010 (Rothfuss et al.) discloses a disposable, endoscopic stapler that is used to place a number of staples at various locations of the placed mesh in order to properly secure the mesh to the tissue. Although the endoscopic stapler is efficient and easy to use for a surgeon, there is a cost issue associated with its use for this type of procedure.

In an effort to alleviate the costs associated with a disposable, multiple fire stapler, some surgeons prefer a re-usable, "single shot" stapler such as disclosed in U.S. Pat. No. 5,246,156 (Rothfuss et al.). Although there is a cost savings to the user, the procedure time is extended when using this type of stapler over the disposable, multiple fire stapler.

In addition to using surgical staplers to secure mesh to inguinal tissue to repair a hernia, other types of fasteners have been developed. One of these fasteners is a helical fastener such as disclosed in U.S. Pat. No. 5,258,000 (Gianturco). This type of fastener is also disclosed in WO 96/03925 (Bolduc et al.). However, although these type of fasteners are also easy to use and decrease the procedure time, cost is also an issue.

Up until now, there is no known procedure and/or device that allows for the repair of tissue defects, such as an inguinal hernia, that is minimally invasive, time and cost effective and easy to use.

SUMMARY OF THE INVENTION

The present invention is a novel method for repairing a defect in tissue as well as a novel prosthetic used in facilitating the method. The method and prosthetic according to the present invention is useful for various types of surgical procedures, and is particularly useful for the repair of an inguinal hernia.

A method according to the present invention for repairing a defect in tissue, such as an inguinal hernia, includes placing a prosthetic over a tissue defect and against the tissue surrounding the defect. Pressure and energy are then applied to the prosthetic to at least one location on the prosthetic and the surrounding tissue until the surrounding tissue and the prosthetic adhere to each other.

A prosthetic according to the present invention comprises three embodiments. A first embodiment of the prosthetic consists of two components. The first component is a plurality of collagen patches which are placed on the tissue surrounding the tissue defect. Any number of collagen pads may be utilized and their selection and placement is typically at the preference of the surgeon. After the collagen pads have been positioned, a patch, typically made of PROLENE™ mesh, is placed over the tissue defect and the collagen pads. The combination of the collagen pads and the placed mesh patch form the prosthetic which is the first embodiment according to the present invention. As mentioned above, force and energy are applied to the patch over each collagen pad for anchoring to the tissue.

A second embodiment of the prosthetic according to the present invention comprises a patch having a plurality of collagen pads integrally formed with the patch. The patch may consist of mesh fibers interwoven with the integrally formed collagen fibers of the collagen pads for forming a single, one-piece prosthetic.

A third embodiment of a prosthetic according to the present invention comprises a patch which is placeable over the tissue defect wherein the patch is made entirely of collagen material throughout. Accordingly, after the patch is placed over the tissue defect and against surrounding tissue, the surgeon has the option to apply force and energy at any desired location of the prosthetic in order to cross-link the fibers of the patch with the fibers of the tissue.

With respect to all three embodiments of the prosthetic according to the present invention, once the prosthetic is placed on the tissue surrounding the tissue defect, pressure and energy are applied to the prosthetic and the tissue surrounding the defect in order to break down the mechanical bonds of both the prosthetic and the tissue for forming new cross-linking of the respective fibers. Accordingly, the prosthetic and the tissue adhere to each other and the prosthetic is fixedly anchored in the tissue aaround and covering the tissue defect in order to provide an effective barrier at the tissue defect.

As it can be well appreciated and understood, the novel method and prosthetics according to the present invention is applicable to many surgical procedures, and more particularly, to a hernia repair surgical procedure for repairing a defect in the tissue of the inguinal anatomy or inguinal hernia.

It is an object of the present invention to provide a method for repairing a defect in tissue that is minimally invasive, time and cost effective and easy to use.

It is another object of the present invention to provide a method for repairing an inguinal hernia that is minimally invasive, time and cost effective and easy to use.

It is another object of the present invention to provide a prosthetic for facilitating the repair of tissue defects that is minimally invasive, time and cost effective and easy to use.

It is another object of the present invention to provide a prosthetic for repairing an inguinal hernia that is minimally invasive, time and cost effective and easy to use.

The various features of novelty which characterize the invention are pointed out with particularity in the claims annexed to and forming a part of the disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DESCRIPTION OF THE PREFERRED EMBODIMENTS

The present invention pertains to the repair of defects in tissue and includes a novel method for repairing tissue defects as well as a novel prosthetic used in facilitating the repair.

By way of example, the present invention is illustrated and described in conjunction with a repair of an inguinal hernia. However, it should be understood that the present invention is applicable to various other surgical procedures that require the repair of defects in tissue.

The Anatomy

Figure 1:
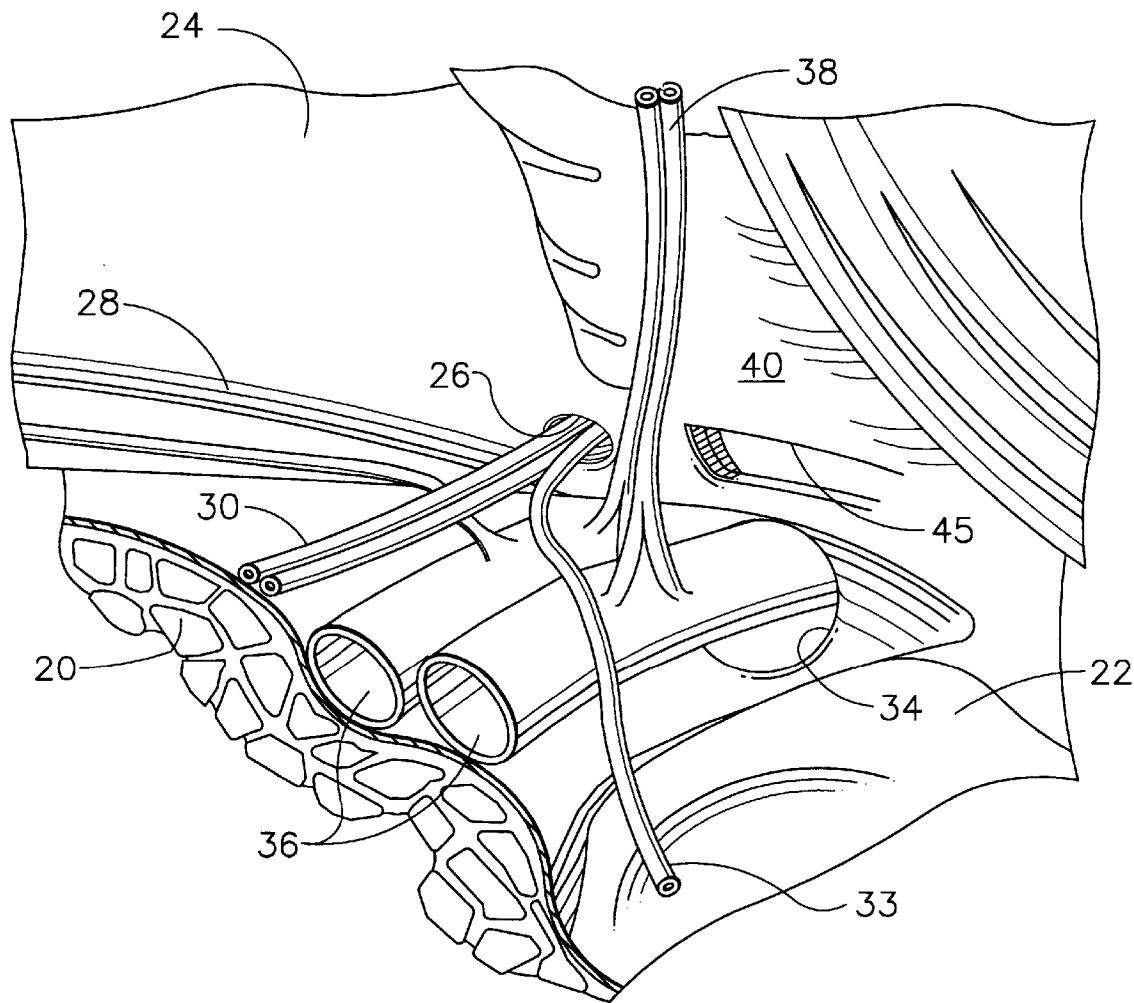
FIG. 1 is a fragmentary perspective view of the lower abdomen particularly the left inguinal anatomy having a defect in the inguinal floor.

Referring now to FIG. 1, one typical application of the present invention is a repair of a defect 45, such as an inguinal hernia, located in inguinal tissue 40 such as the inguinal floor. The delicate anatomical structures of the left inguinal anatomy of a human patient are illustrated in order to particularly point out the usefulness of the present invention.

Generally, the inguinal hernia 45 is accessible through abdominal muscle 20. As can be well appreciated, an extremely sensitive network of vessels and nerves exist in the area of a typical inguinal hernia 45, which requires a surgeon to conduct a hernia repair with great skill and caution.

For instance, in the transverse abdominis aponeurosis 24, an internal ring 26 permits gastric vessels 30 and Vas deferens 33 to extend therethrough over an edge of inguinal ligament 28. Femoral canal 34 is located near Cooper's ligament 22 and contains external iliac vessels 36 and inferior epigastric vessels 38.

In many cases, the edge of the inguinal ligament 28 and Cooper's ligament 22 serve as anatomical landmarks and support structures for supporting surgical fasteners such as those mentioned previously. The area containing the external iliac vessels 36 and the Vas deferens 33 is commonly known to surgeons as "the Triangle of Doom". Accordingly, it is critical that the surgeon avoid injuring any of these vessels described above and extreme care must be taken when performing dissection, suturing or stapling within this area.

The Devices

FIGS. 2–5 illustrate three embodiments of a prosthetic according to the present invention that are used to enable a novel surgical procedure.

Figure 2:
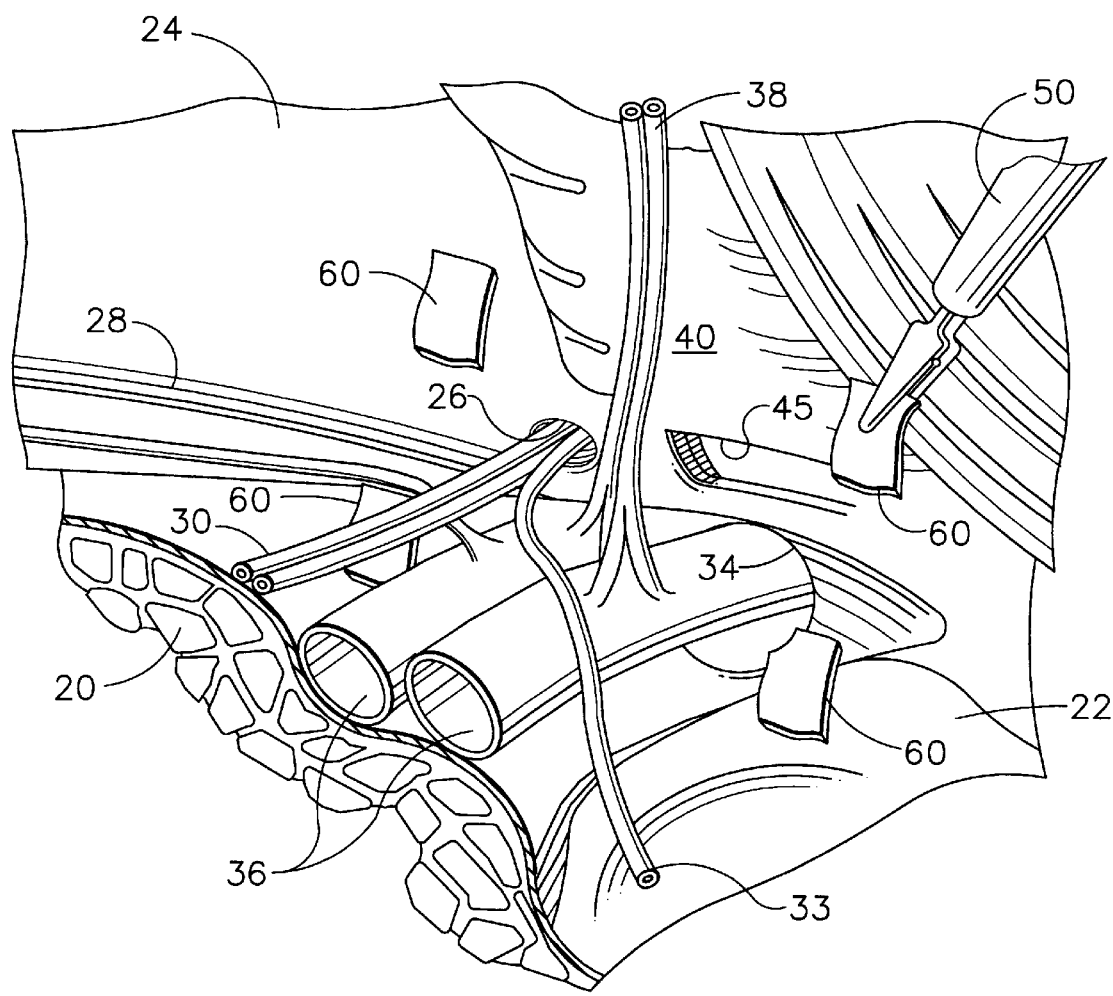
FIG. 2 is a fragmentary perspective view of the lower abdomen of FIG. 1 illustrating the placement of collagen pads in preparation for repair of the defect in accordance with the present invention.

FIG. 2 shows a plurality of collagen pads 60 which can be sized at the preference of the surgeon prior to placement around the defect 45 on surrounding tissue such as Cooper's ligament 22, the edge of the inguinal ligament 28, the inguinal floor 40, etc.

Figure 3:
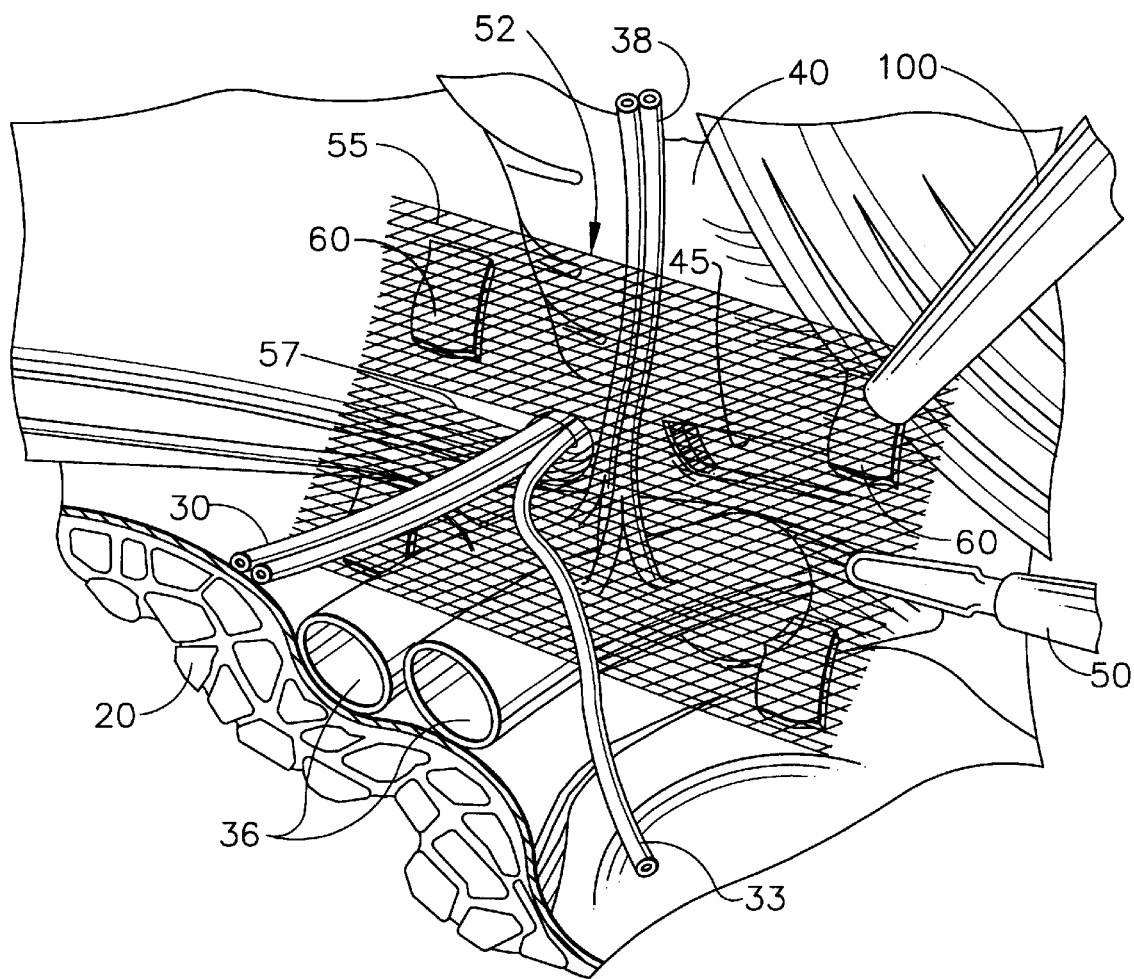
FIG. 3 is a fragmentary perspective view of FIG. 2 illustrating the placement of a mesh patch over the collagen pads for securing to tissue through the use of an energy delivery device in accordance with the present invention.

As illustrated in FIG. 3, the collagen pads 60 are designed to interface with tissue surrounding the tissue defect 45 and a patch 55 to form a two-piece prosthetic 52. The patch 55 may consist of any desired configuration, structure or material. However, the patch 55 is preferably made of PROLENE™ (a known polymer made up of fibers) and preferably configured as mesh. It is within the training and comfort zone for surgeons to use the PROLENE™ mesh patch 55 since the patch 55 is easily sized, such as providing a side slot 57, for accommodating the gastric vessels 30 and the Vas deferens 33.

As illustrated, the patch 55 is placeable over the defect 45 and the collagen pads 60 for providing a sufficient barrier to internal viscera (not shown) of the abdomen which would otherwise have a tendency to protrude through the defect 45 and cause the patient a great deal of pain and discomfort.

The pads 60 are strips of material or mesh made of collagen fiber which are constructed of either man-made or natural collagen fibers. The fibers of the collagen pads 60 are made of long polymer chains that are bundled together through crosslinking to form fibers. One type of collagen that has been found to be useful for the pads 60 is glutaraldehyde cross-linked bovine pericardium (PERI-STRIPS™ manufactured and sold by BioVascular, Inc.). This material is rich in collagen and particularly useful in the present invention.

Moreover, as is well known, collagen makes up the structural support of the extracellular matrix in most human tissue and also consists of polymer fibers.

When energy is applied to all of these fibers, the cross-links are broken and the fibers become "frayed" on their ends. The term "energy" refers to the application of either radio frequency (RF) electricity, ultrasound (acoustic/mechanical) energy, laser (coherent light) energy, ultraviolet light (electromagnetic) energy, microwave (electromagnetic) energy, white light (non-coherent light) energy or the like or any combinations of the above.

When pressure or force is used to apply the collagen pads 60 to other polymer or tissue surfaces, e.g. the patch 55 and the tissue, these frayed ends are brought into intimate contact with the polymer chains that make up these other surfaces. The term "pressure" refers to the application of a force applied by any type of instrument or object to the collagen pads 60 and the patch 55 over the cross sectional area of the contact surface of these instruments or objects.

The frayed fiber ends of the collagen pads 60 then recross-link with the polymer chains of the patch 55 and the tissue due to their close proximity to each other. This cross-linking between chains forms a mechanical bond of sufficient strength to hold the collagen pads 60 to both the polymer mesh patch 55 and to the tissue surrounding the defect 45. Accordingly, the collagen pads 60 and patch 55 become mechanically linked or bonded to any object that has sufficient polymer properties to form a new cross-link, (i.e. most human tissue). Accordingly, upon applying energy and pressure to the collagen pads 60, the patch 55 and the tissue, they adhere to each other thereby anchoring or fixating the prosthetic 52 to the tissue. This makes choice of placement of the prosthetic 52 easy, since it can be attached to most structures in the area of the defect 45 without causing any sub-surface damage to the delicate anatomical structures. In addition, the collagen that makes up the pads 60 will be replaced over time by human connective tissue making this aspect of the prosthetic 52 absorbable.

Figure 4:
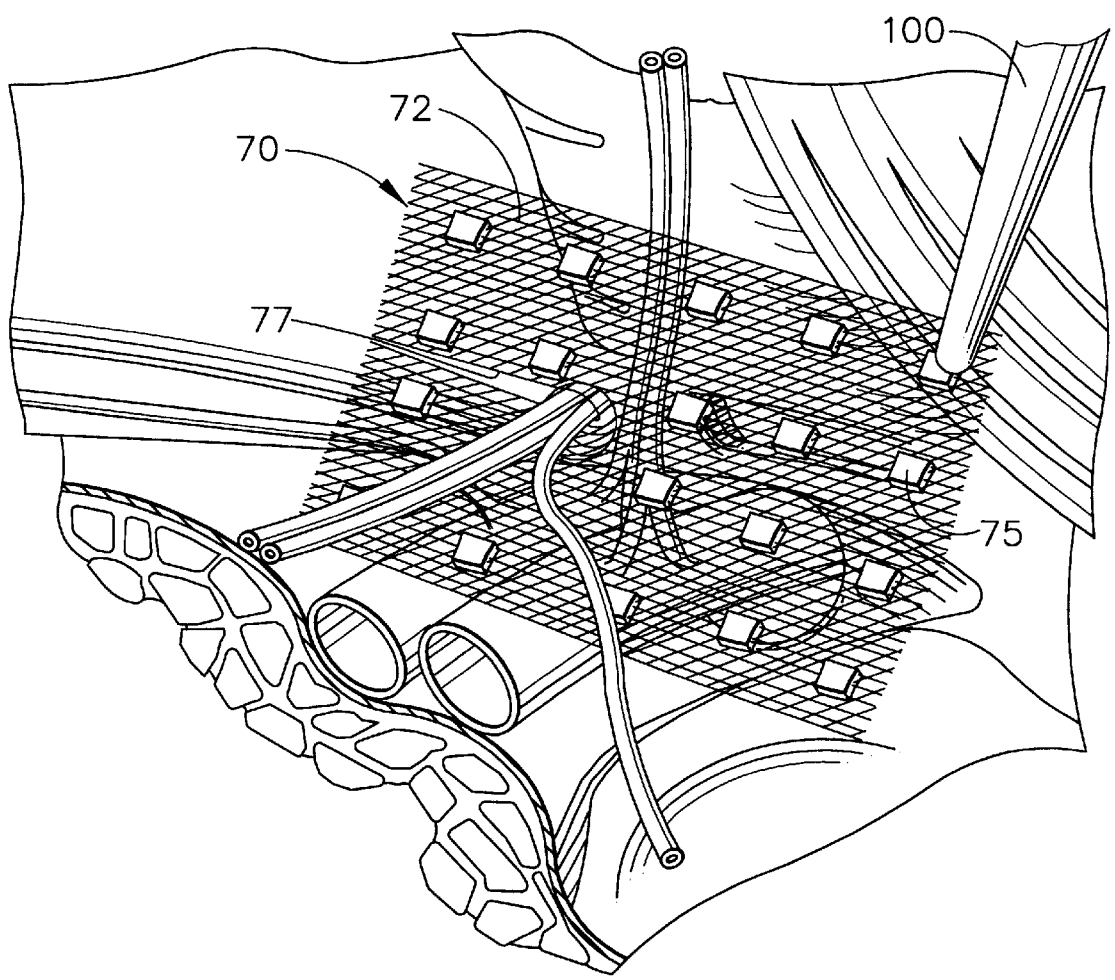
FIG. 4 is a fragmentary perspective view of an alternate embodiment of a hernia prosthetic according to the present invention wherein the mesh patch is provided with integral pads of collagen.

FIG. 4 illustrates a second embodiment of a prosthetic 70 according to the present invention. The prosthetic 70 includes a patch 72 similar to the mesh patch 55 (FIG. 3) described above. However, the patch 72 includes a plurality of collagen pads 75 that are integrally formed in the patch 72. The collagen pads 75 are interwoven and/or integrally combined with the mesh fibers of the patch 72. It is also envisioned that the collagen pad 75 may consist of one or more collagen strands or elongated fibers that are integrally woven with the fibers of the mesh patch 55, e.g. PROLENE™ fibers, in an alternating pattern or other desired pattern. The prosthetic 70 also has the ability to be sized to any dimension or configuration desired by the surgeon and has the ability to permit a side slot 77 to be cut into the patch 72 for accommodating delicate vessel structures or the like.

Figure 5:
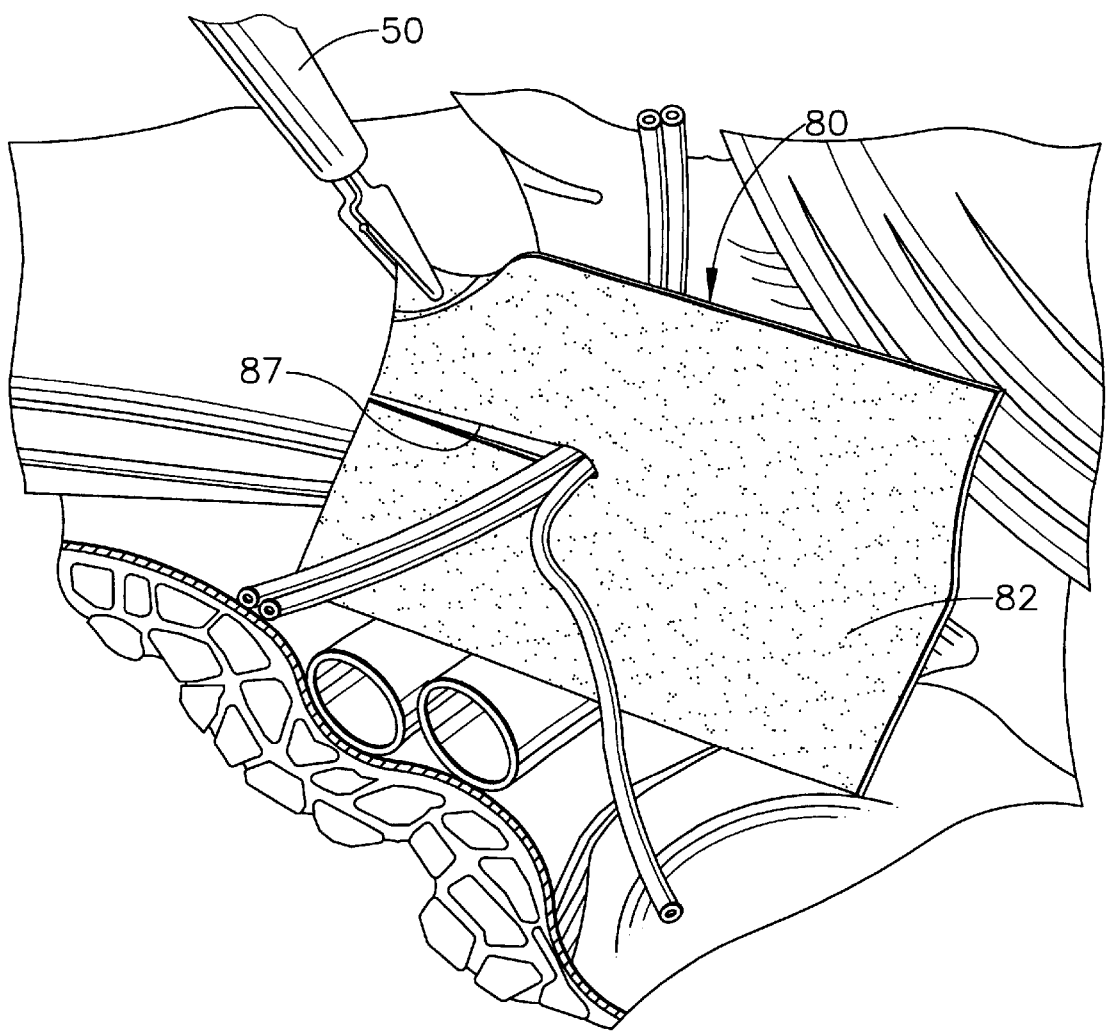
FIG. 5 is a fragmentary perspective view of another alternate embodiment of a hernia prosthetic according to the present invention wherein the prosthetic is made of collagen.

FIG. 5 illustrates a third embodiment of a prosthetic 80, according to the present invention, which is a patch 82 comprising collagen material throughout. Again, the collagen patch 82 is sized and configured according to preference and accommodates a side slot 87 if the surgeon desires this feature.

The Method

Although the present invention is applicable to various surgical procedures involving the curing or repairing of tissue defects, the method according to the present invention is illustrated in FIGS. 2–5 in accordance with the repair of an inguinal hernia 45 located in the left inguinal region of a human patient.

As best shown in FIG. 2, in repairing a tissue defect 45, the surgeon accesses the defect 45 with caution and carefully identifies the anatomical structures and landmarks as well as the tissue surrounding the defect 45 such as the inguinal floor 40, aponeurosis 24, Cooper's ligament 22, etc. Additionally, if any internal viscera had extended through the defect 45, the surgeon gently moves the viscera back through the defect 45 and into the abdominal cavity. The surgeon then determines the location for placement of the collagen pads 60 on the tissue surrounding the defect 45. The collagen pads 60 are placed on the tissue around the defect 45 using an instrument 50 such as standard forceps or laparoscopic graspers if the repair is being conducted with the aid of an endoscope as part of laparoscopic procedure.

At the surgeon's preference, the surgeon may use one or several collagen pads 60 for strategic placement on the tissue surrounding the defect 45. Additionally, the surgeon may opt to customize the size and configuration of each collagen pad 60 to take into account the unique anatomical structures encountered. For instance, a corner of one of the collagen pads 60 may be removed for accommodating the external iliac vessels 36.

After pre-positioning the collagen pads 60, the surgeon introduces the patch 55 into the surgical site at the defect 45 as shown in FIG. 3. The patch 55 which may be standard PROLENE™ mesh, is sized and configured, for a customized fit at the site and is placed over the defect 45 and each collagen pad 60. Again standard forceps 50 are used to introduce and place the mesh patch 55. The side slot 57 is used to accommodate vessel structures 30 and 33 in a safe and convenient manner. Accordingly, the gastric vessels 30 and the Vas deferens 33 are positioned in the side slot 57 and surrounded by the remainder of the mesh patch 55.

Once the patch 55 is placed over the defect 45 and the collagen pads 60, an energy-based device 100, such as an RF electrosurgical device, is placed on the patch directly over each collagen pad 60 in order to form the prosthetic 52. The energy device 100 is then used to apply force and energy to the patch 55 and the pads 60 sufficient enough to denature or break the mechanical bonds of the patch 55, the collagen pads 60 and the tissue. As mentioned above, new cross-linking occurs between the tissue, the collagen pads 60 and the patch 55 to ensure that the tissue and the prosthetic 52 adhere to each other. With newly formed cross-linking of the fibers of the prosthetic 52, e.g. the collagen pads 60 and the patch 55 and the tissue surrounding the defect 45, the prosthetic 52 is anchored over the defect 45 and fixedly attached to the surrounding tissue. Accordingly, a sufficient barrier is provided to the defect 45 and internal viscera are prevented from entering through the defect 45.

It can also be appreciated that the prosthetic 70 (FIG. 4) and prosthetic 80 (FIG. 5) are used in a similar manner to that described above. When utilizing the prosthetic 70 with integrally formed collagen pads 75 in the mesh patch 72, the surgeon performs a single placement step for the prosthetic 70 by placing the prosthetic 70 over the tissue defect 45 as opposed to the two step placement step with the prosthetic 52 (FIGS. 2 and 3) outlined above. Moreover, in utilizing the prosthetic 70, the surgeon may optionally utilize any number of the integrally-formed collagen pads 75 for adhering the prosthetic 70 to the tissue.

Additionally, the prosthetic 80 (FIG. 5) is another convenient device for facilitating the repair of the defect 45 because it allows the surgeon to select any desired location on the prosthetic 80 itself to apply the force and energy for to anchoring the prosthetic 80 to the tissue because the patch 82 itself is made of collagen material throughout.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A prosthetic for placement over a defect in tissue comprising:

a plurality of individual collagen pads, said collagen pads being customizable in size and configuration for pre-positioning on tissue surrounding said defect; and a patch separate from said plurality of individual collagen pads said patch being placeable over said defect and said plurality of individual collagen pads, wherein said plurality of individual collagen pads, said patch and said tissue are adhereable to each other upon an application of pressure and energy.

2. The prosthetic according to claim 1, wherein said patch is mesh.

3. The prosthetic according to claim 2, wherein said patch is made of PROLENE™.

4. A prosthetic for placement over a defect in tissue comprising:

a mesh patch; and a plurality of individual collagen pads integrally formed with said patch.

5. The prosthetic according to claim 4, wherein said patch is made of PROLENE™.

6. The prosthetic according to claim 5 wherein said plurality of collagen pads integrally formed with said patch consist of at least one collagen strand.

7. The prosthetic according to claim 6 wherein said at least one collagen strand is integrally woven with said patch.

* * * * *